United States Patent [19]

Walter

[11] 4,133,203

[45] Jan. 9, 1979

[54] APPARATUS FOR TESTING THE BURST STRENGTH OF A LINE OF PERFORATIONS

[75] Inventor: Alfred Walter, Schlieren, Switzerland

[73] Assignee: Alfred Walter AG, Schliern, Switzerland

[21] Appl. No.: 867,622

[22] Filed: Jan. 6, 1978

[30] Foreign Application Priority Data

Jan. 10, 1977 [CH] Switzerland ............................ 258/77

[51] Int. Cl.² ............................................. G01N 3/32
[52] U.S. Cl. ...................................................... 73/838
[58] Field of Search ............................ 73/102, 98, 101

[56] References Cited

U.S. PATENT DOCUMENTS

| 1,920,039 | 7/1933 | Thwing | 73/98 |
| 2,983,139 | 5/1961 | Galbraith et al. | 73/102 |

*Primary Examiner*—Jerry W. Myracle
*Attorney, Agent, or Firm*—Fitch, Even, Tabin & Luedeka

[57] ABSTRACT

Apparatus for testing the burst strength of a line of perforations in a sheet of paper. The testing apparatus comprises a first means fixedly mounted in a frame for gripping a sheet of paper on one side of a line of perforations extending across the paper and a second means rotatably mounted in the frame in spaced relation to the first means for gripping the paper on the other side of the line of perforations. A pendulum is attached to the second means so that swinging of the pendulum causes rotation of the second means. The pendulum may be swung along a path which extends from a first position, where energy is stored in the pendulum, through a second position, where the paper is rendered taut and the line of perforations is burst by the energy stored in the pendulum, to a third position, where the energy remaining in the pendulum after the bursting action is dissipated. An indicating means is provided which is actuated by the pendulum for indicating the amount of energy remaining in the pendulum after the bursting action. An apparatus is also provided for providing various different lines of perforations in a paper sample for use in the testing apparatus.

10 Claims, 10 Drawing Figures

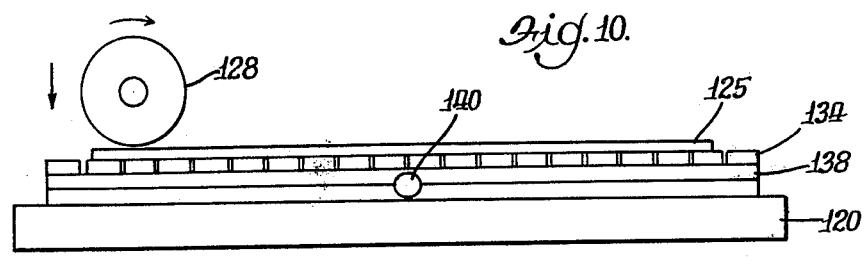
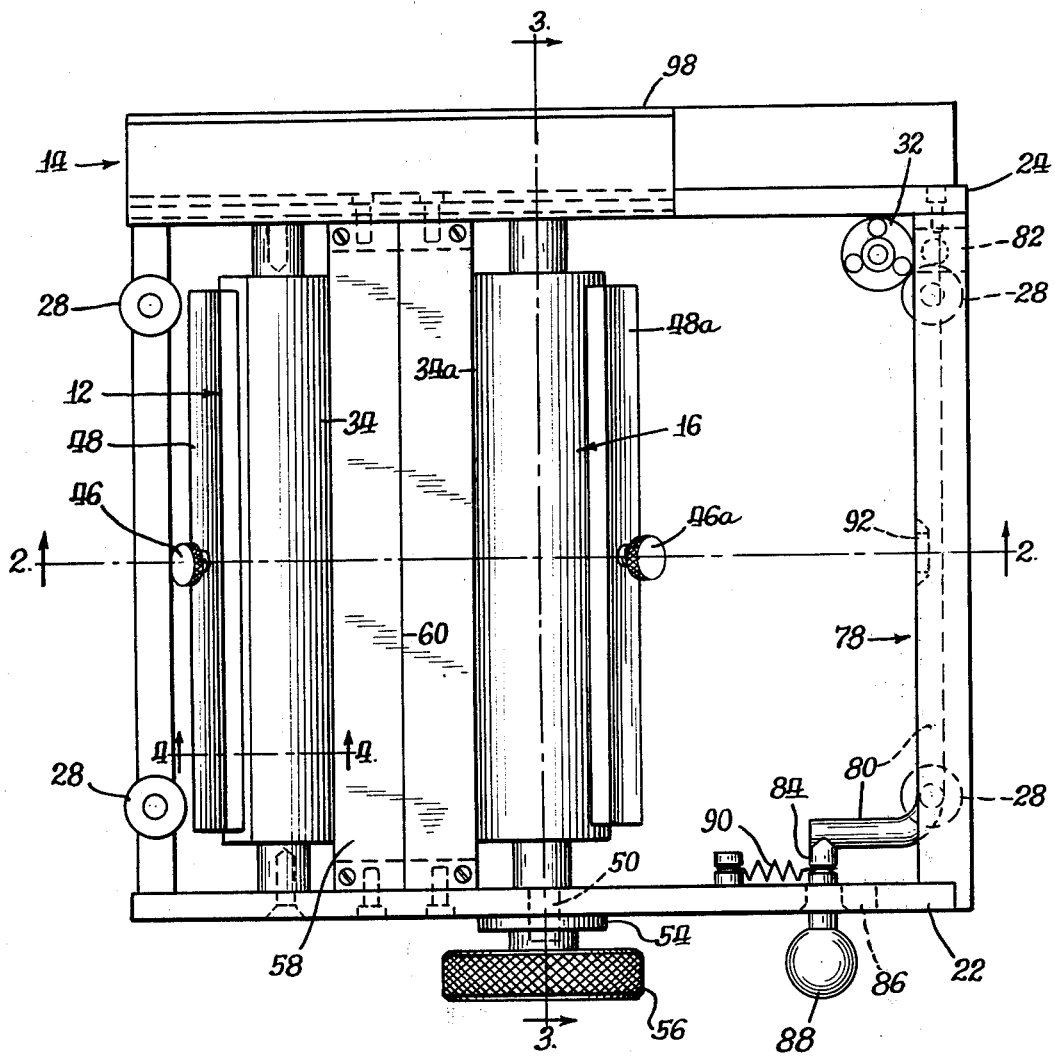
Fig. 10.
Fig. 1.

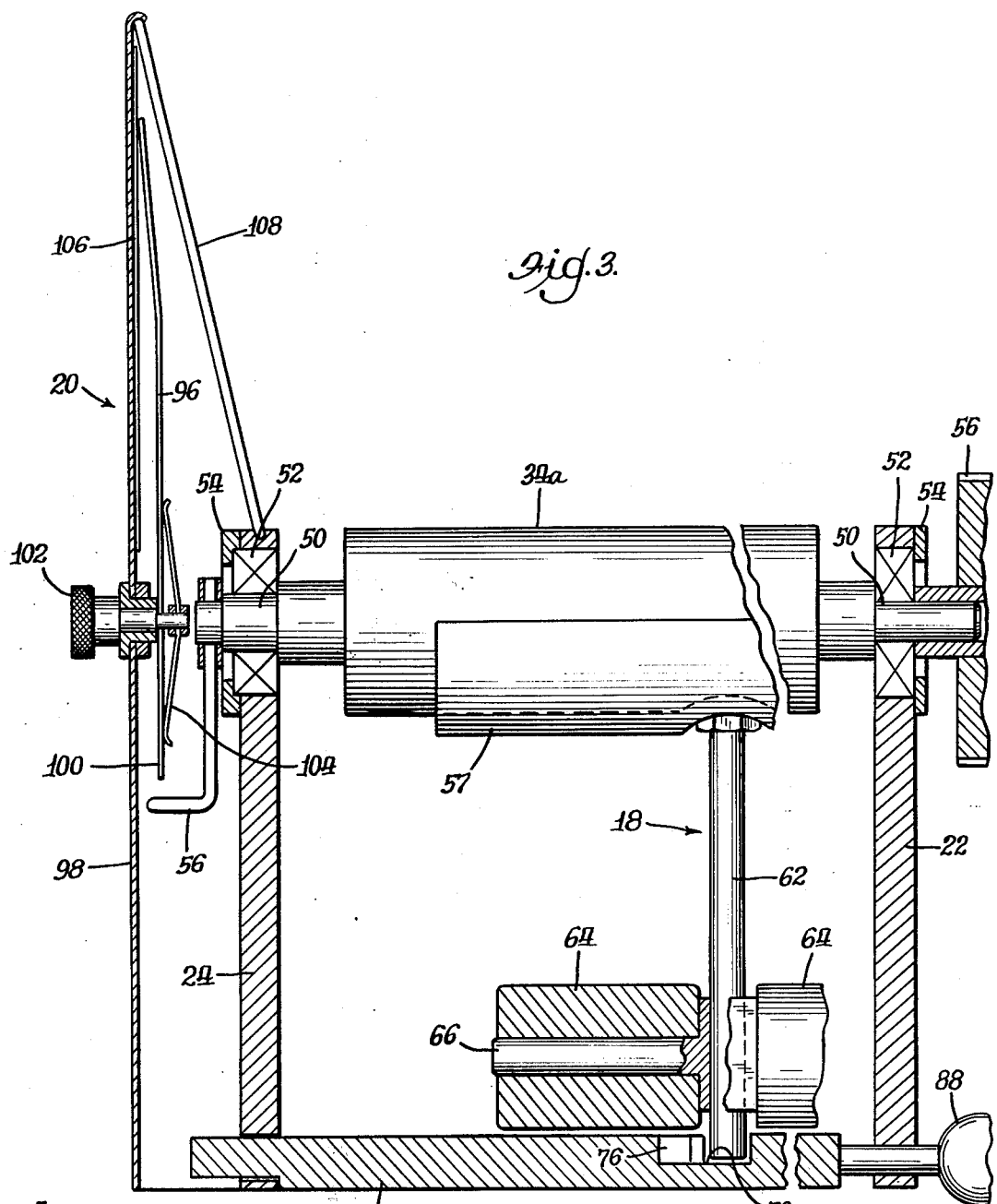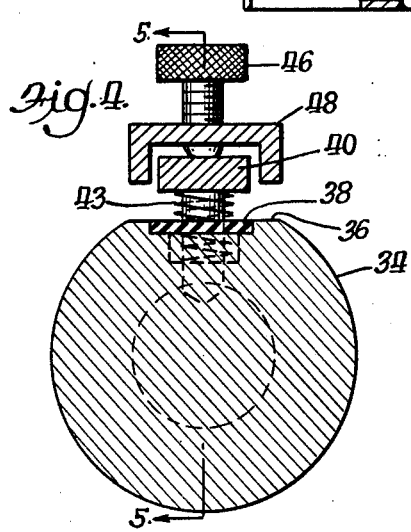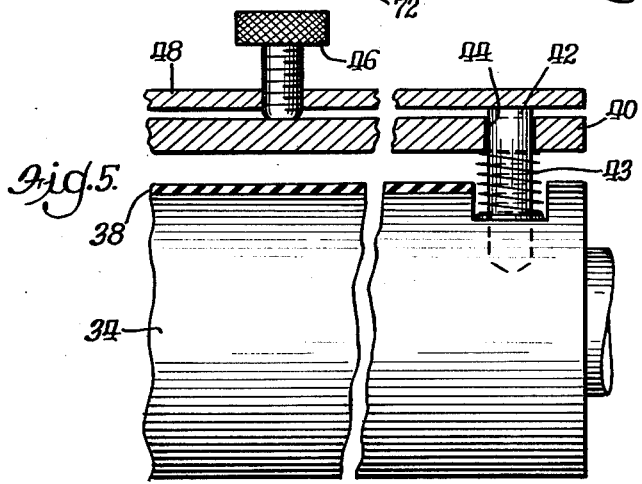

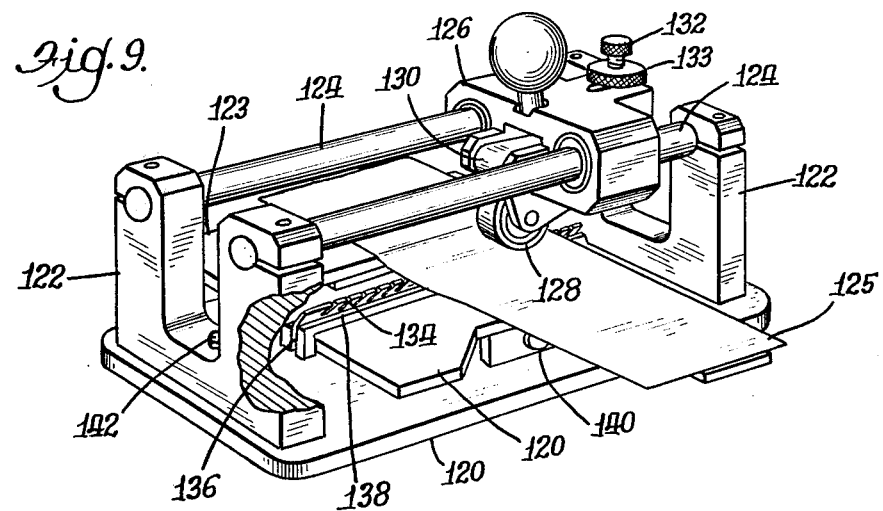
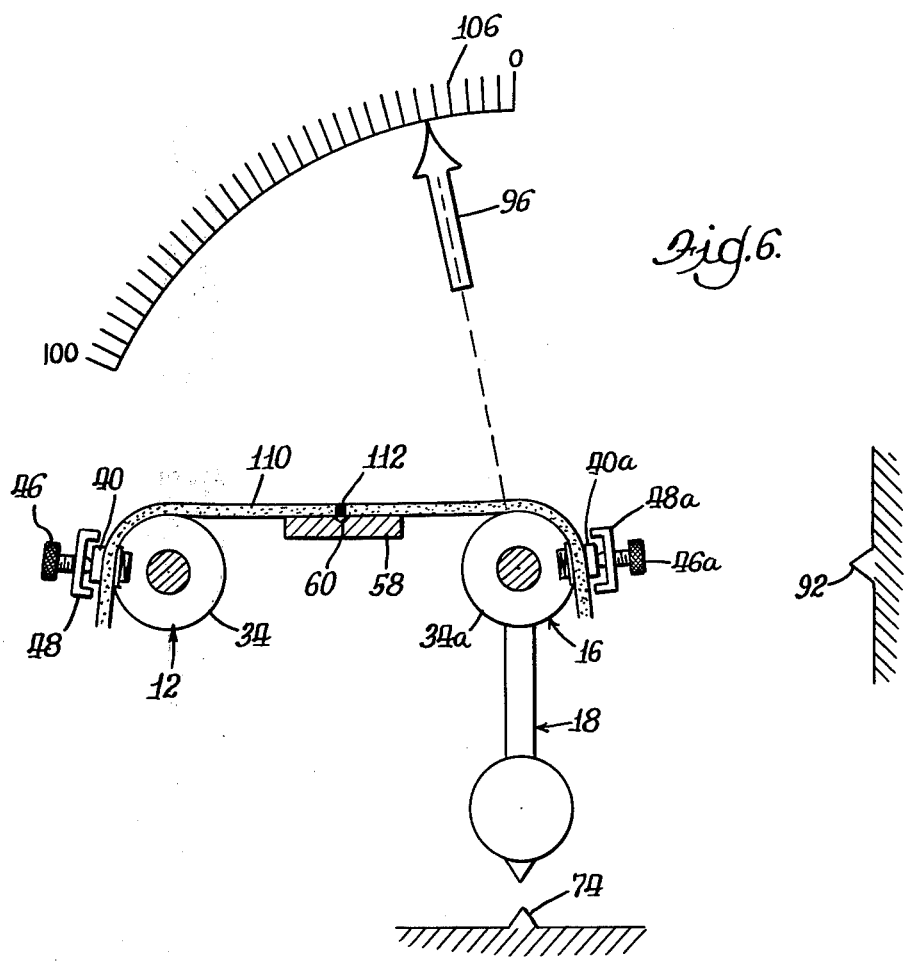

APPARATUS FOR TESTING THE BURST STRENGTH OF A LINE OF PERFORATIONS

The present invention relates to testing apparatus and more particularly to an apparatus for testing the burst strength of a line of perforations in paper or simulated papers.

Continuous forms, such as electronic digital processing (EDP) listing paper, normally contain lines of perforations which extend across the continuous form and serve as folding lines as well as separation lines of the individual forms. Other lines of perforations, which extend along the form, are found in snapout and EDP listing paper. These with-the-web perforations serve as stub removals for EDP testing paper and internal vertical perforations on EDP listing paper or snap-out sets. Normally, the lines of perforation are made in the printing press after the actual printing of the form.

A common problem with such continuous forms is that the lines of perforations are too strong or too weak which can disturb the work of the forms user. If the perforations are too weak, the forms will burst in the printer of the computer. If, on the other hand, the perforations are too strong, the burster will not be able to separate the individual forms as desired and they may not refold in the computer stacker. This is also true of the vertical or with-the-web perforations which, when made too strong, will not come apart during the snap-apart operation of the "snap-out" set or if too loose, will prematurely fall apart. The burst strength of the line of perforations of a continuous or other form thereby should match the users methods of forms handling in order to give optimal results.

The desired burst strength of the lines of perforation, is affected by the machinery installed at the users plant, for example, printers and bursters, as well as by the paper strength and the folding units on the printing presses and collators. The burst strength of a line of perforation is determined by the ratio of cut and tie of a perforation in the line of perforations, by the sharpness of the perforating blade or wheel, the pressure of the perforator, and the paper quality. Two different production runs of the same type of paper, perforated under equal conditions, can give distinctly different results.

Therefore, it is important to enable production control at a forms printer to be in possession of precise and comparable figures in order to check continuously the burst strength in the production and to adjust it according to the forms users needs. Previously, this was not possible because the burst test was usually executed by hand and the setting of the machines was done in an empiric way and on the basis of general know-how. Test apparatus has been proposed which stretches an inserted sample of paper with a continuously increasing pull up to a point where the paper breaks at the line of perforations and a figure is then read on a scale. However, the figures obtained on this test apparatus differed very much and the results were not satisfactory because the constant pull does not match the actual tearing or bursting action in the users forms handling or high speed printers. In a printer, the continuous forms are often exposed to sudden pulls (for example, if there is a high speed eject) and also very irregularly changing pull energy. In the forms handling equipment, such as bursters, the separation occurs by a sudden pull on the individual forms and not by a steady stretching of the form.

An object of the present invention is to provide an apparatus for testing the strength of a line of perforations. Another object is the provision of an apparatus for testing the strength of a line of perforations by which precise and comparable figures can be established for production control at the forms producer plant.

Other objects and advantages of the present invention will become apparent by reference to the following description and accompanying drawings wherein:

FIG. 1 is a plan view of a perforation test apparatus constructed in accordance with the present invention;

FIG. 3 is an enlarged vertical cross-sectional view taken generally along line 3—3 of FIG. 1 with portions being broken away;

FIG. 4 is an enlarged cross-sectional view taken generally along line 4—4 of FIG. 1, but rotated 45° clockwise;

FIG. 5 is a cross-sectional view taken generally along line 5—5 of FIG. 4;

FIGS. 6 through 8 are schematic views similar to FIG. 2 showing the operation of the apparatus shown in FIGS. 1 through 5;

FIG. 9 is a perspective view of the perforating apparatus useful with the perforation test apparatus shown in FIGS. 1 to 8; and FIG. 10 is a schematic view of the perforating apparatus shown in FIG. 9.

Figure 2:
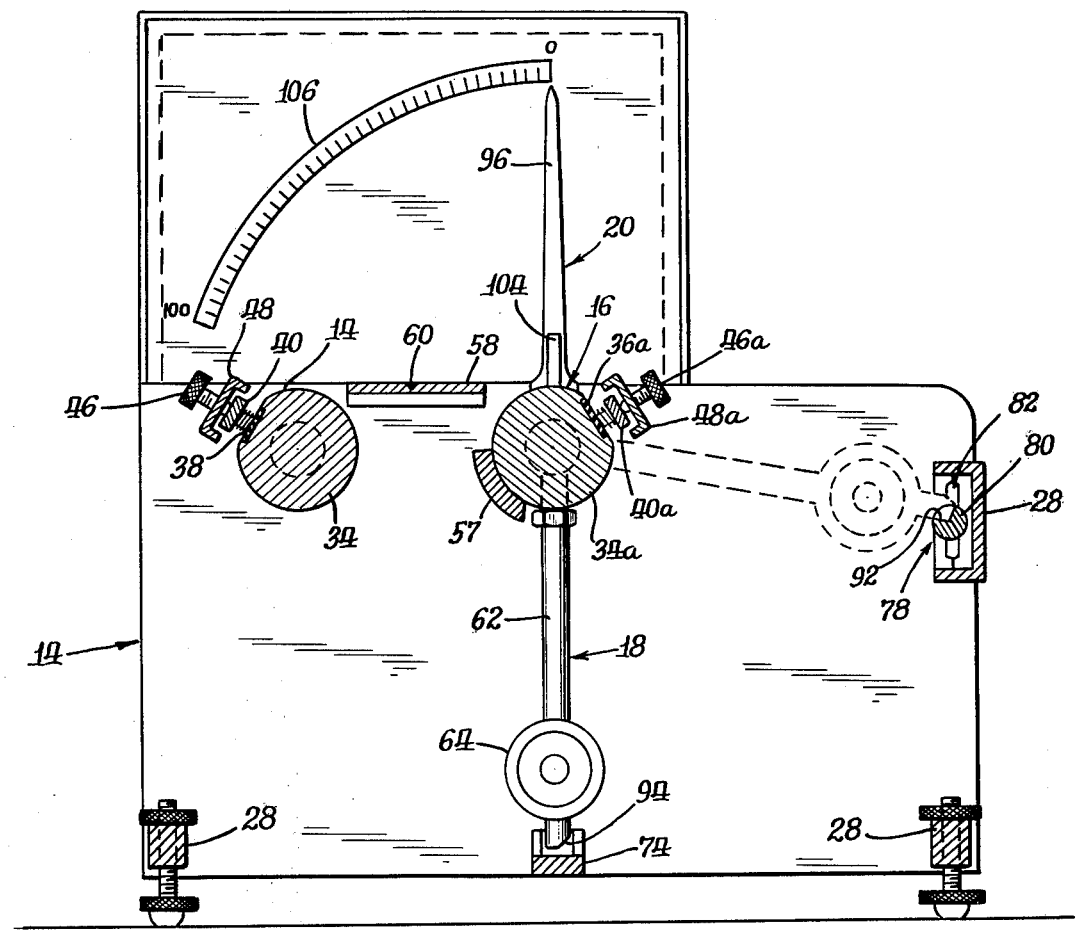
FIG. 2 is a vertical cross-sectional view taken generally along line 2—2 of FIG. 1.

Generally, in accordance with the present invention perforation test apparatus is provided for testing the burst strength of a line of perforations in a sheet of paper. The test apparatus illustrated in FIGS. 1 to 8 comprises a first means 12 fixedly mounted in a frame 14 for gripping a sheet of paper on one side of a line of perforations extending across the paper. A second means 16 is rotatably mounted in the frame 14 in spaced relation to the first means 12 for gripping the paper on the other side of the line of perforations. A pendulum 18 is attached to the second means 16 so that swinging of the pendulum causes rotation of the second means. The pendulum 18 may be swung along a path which extends from a first position, where energy is stored in the pendulum, through a second position, where the paper is rendered taut and the line of perforations is burst by the energy stored in the pendulum, to a third position, where the energy remaining in the pendulum after the bursting action is dissipated. An indicating means 20 is provided which is actuated by the pendulum 18 for indicating the amount of energy remaining in the pendulum after the bursting action.

More particularly, as shown particularly in FIGS. 1 to 3, the testing apparatus includes the frame 14 which includes two spaced, parallel extending rectangular bearing plates 22 and 24. The plates 22 and 24 are maintained in spaced relation by horizontally extending bars 26 suitably attached to the lower corners of the rectangular plates and a horizontally extending U-shaped channel 28 suitably attached to the plates at the right margins thereof close to the top edges. The housing 14 is leveled by four adjustable supports 30 disposed in the bars 26 at the respective corners of the housing. A sight level 32 is suitably mounted on the back plate 24.

The first gripping means 12 includes a cylinder 34 which extends horizontally between and is fixedly attached to the front and back plates 22 and 24 in the upper part of the housing 14. As shown particularly in FIGS. 2, 4 and 5, the cylinder 34 is provided with a flat surface 36 and a pad 38 of rubber is inlayed in the surface. The paper is pressed against the pad by a press bar 40 which extends parallel to the pad 38 and has a rough lower surface. The press bar is guided in its movement to and from the pad by a pair of guide pins 42 extending through holes 44 in the ends of the bar 40 and suitably attached to the cylinder 34. The press bar 40 is biased away from the pad 38 by a pair of springs 43 disposed about the guide pins 42. The press bar 40 is pressed against the pad 38 by a screw 46 that is threaded into a U-shaped holding bar 48 that covers the press bar 40 and is mounted in spaced relation to the cylinder 34 by the guide pins 42. The screw 46 is disposed so as to bear against the press bar at a position intermediate its ends.

In the illustrated embodiment the second gripping means 16 is similar in construction to the first gripping means 12 and similar parts are indicated with the same reference numeral with the subscript "a". The difference between the second gripping means 16 and the first gripping means 12 is that the cylinder 34a is rotatably mounted to the front and back plates 22 and 24. In this connection, reduced end portions 50 of the cylinder 34a extend through the front and back plates 22 and 24 and, as shown in FIG. 3, are rotatably mounted therein by respective bearings 52. The bearings 52 are retained in position by respective bearing retainers 54. The reduced end portion 50 at front end of the turnable cylinder 34a extends through the front plate 22 and its front end is provided with a wheel 56, which is fixed thereto. The back end of the reduced end portion 50 at the back end of the turnable cylinder 34a is reduced in diameter and extends beyond the back plate 24. An L-shaped lever 56, the purpose of which will be explained hereinafter, is anchored to the back end and is shown in FIG. 3 rotated approximately 90° counterclockwise to better show its construction. The weight of the press bar 40a and the U-shaped housing 48 is counterbalanced by an arcuate plate 57 which is attached to the rotatable cylinder 34a diametrically opposite the pad 36a.

Disposed midway between the two cylinders 34 and 34a is an elongated plate 58 which is fixedly mounted to the front and back frame plates 22 and 24 so that its surface is parallel to the upper surfaces of the cylinders 34 and 34a. As shown in FIG. 1, a reference line 60 is engraved on the plate 58 parallel to the cylinders to serve as a position line for the line of perforations on the sample paper being tested.

As shown in FIGS. 2 and 3, the pendulum 18 is attached to the turnable cylinder 34a. In this connection, the pendulum 18 includes a rod 62 which is suitably connected at its upper end to the turnable cylinder 34a intermediate its ends. The pendulum 18 further includes a pair of tubular weights 64 which are fixedly disposed on weight holder rods 66 which extend perpendicular to and are fixedly attached to the lower end of the pendulum rod 62.

A locking device 68 is provided for locking the pendulum 18 in its rest position during the insertion of paper or during transportation of the test apparatus so that vibrations do not distort its accuracy. As shown in FIGS. 2 and 3, the lower end of the pendulum rod 62 extends below the tubular weights 64. In the unlocked condition, the lower end of the pendulum rod 62 passes through a slot 72 in an elongated locking bar 74 that extends through the front and back plates 22 and 24.

The locking bar 74 is moveable from outside the front plate and, when the locking bar 74 is in its forward most position, the lower end of the pendulum rod 62 is captured in a matching recess 76 in the top of the locking bar 74.

The pendulum 18 is locked in its energy storage position, wherein the pendulum is almost horizontal as shown by dotted lines in FIG. 2, by a releasable snap-in device 78. The snap-in device 78 includes an L-shaped rod 80 disposed within the channel 28. The rear end of the rod 80 is seated in a bearing block 82 mounted within the channel 28 adjacent the inside surface of the rear plate 24, which bearing block 82 permits horizontal rotation of the L-shaped rod 80. The front end of the rod 80 is attached to a horizontal rod 84 that extends through a slot 86 in the front plate 22 and is provided with a knob 88. The L-shaped rod 80 is biased toward the pendulum 18 by a spring 90 mounted on the inside surface of the front plate 22. A notch 92 is provided in the middle of the L-shaped bar 80 for receiving the lower end of the pendulum rod 62. A ramp 94 (FIG. 2) is provided on the lower end of the pendulum rod 62 to permit the pendulum rod to be snapped into the notch 92. The pendulum 18 is released by moving the knob 88 away from the pendulum 18. An adjustable plate (not shown) may be provided on the lower surface of the notch 92 to permit adjustment of the energy stored in the pendulum.

The energy remaining in the pendulum after bursting the paper is indicated by the indicating means 20 which includes, as shown in FIGS. 2 and 3, an indicating needle 96 rotatably mounted to a vertical plate 98 which extends above the rear plate 24 and is mounted in spaced relation to the rear plate 24 of the frame. The center of rotation of the indicating needle 96 is on line with the center of rotation of the turnable cylinder 34a. The needle 96 is provided with an extension 100. A knob 102 is provided on the rear surface of the mounting plate 98 which knob is connected to the needle for manually rotating the needle 96. A leaf spring 104 bears against the front of the needle 96 and its extension 100 to thereby serve as a friction drag on the needle. A readout scale plate 106 is disposed on the front surface of the mounting plate 96 which readout scale 106 is provided with indicating lines. The readout scale 106 and needle 96 are covered with a Plexiglass cover 108.

The needle 96 is engaged by the L-shaped bolt 56 that is positioned so that, when the pendulum is passing through its rest position, the needle points to the 100% mark on the scale 106. The scale is proportioned so that the needle points to 0.0% when the pendulum reaches its highest position with no sample paper being tested. For proper adjustment the L-shaped bolt 56 should be rotated about 90° clockwise from its position illustrated in FIG. 3.

Figure 7:
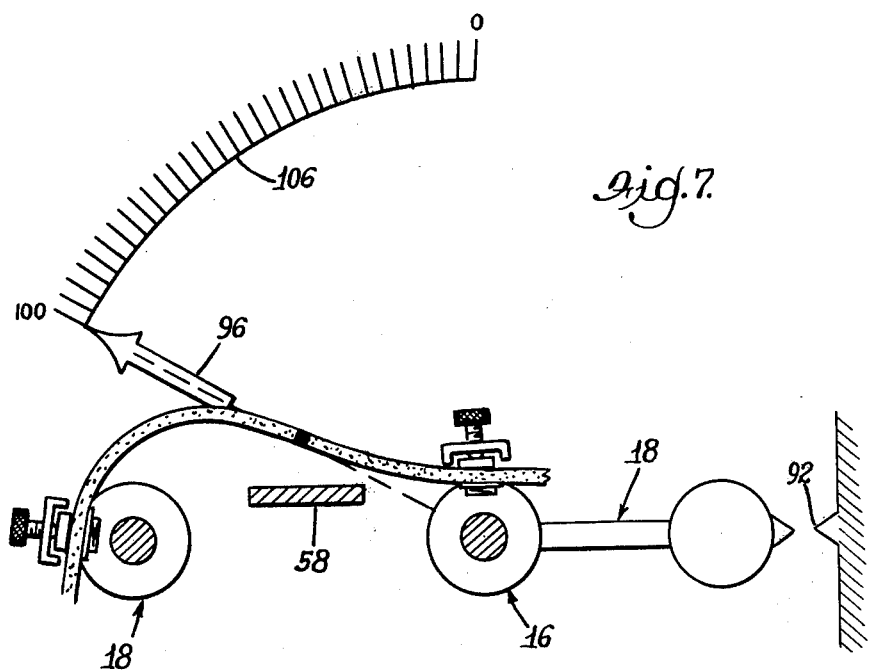
Figure 8:
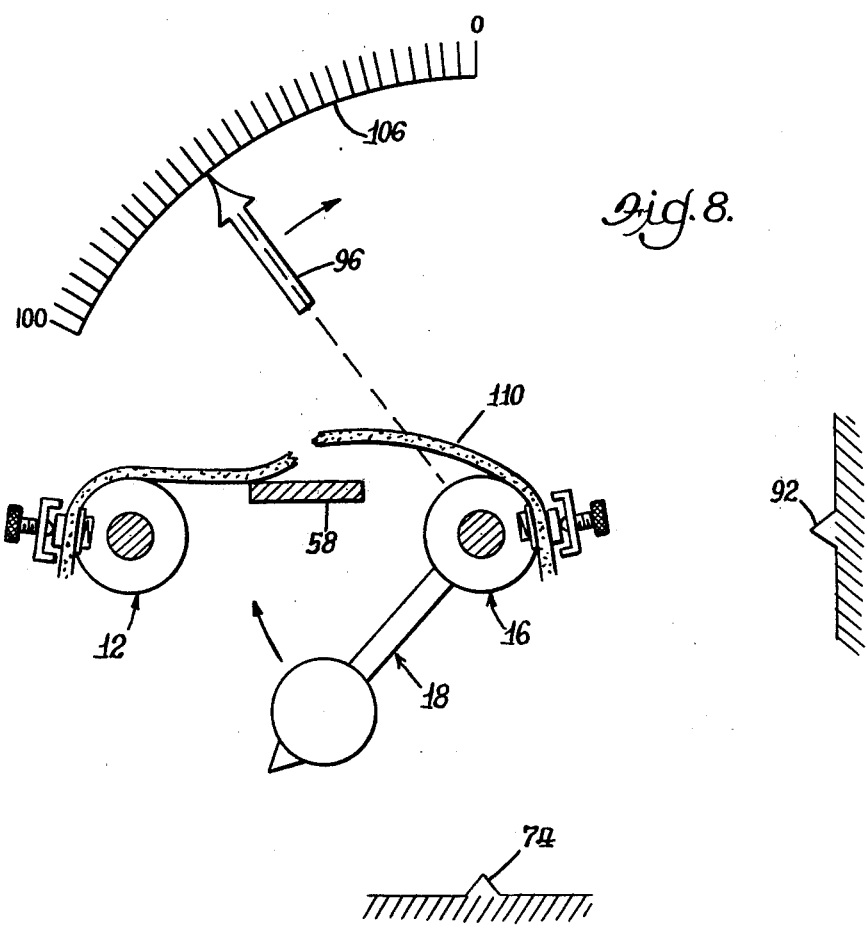

FIGS. 6 through 8 schematically show the testing apparatus in operation. Initially, the ends of a sample paper 110 are inserted under the press bars 40 and 40a of the two gripping means 12 and 16. The paper 110 is then adjusted so that a line of perforations 112 therein extends parallel to the reference line 60 on the flat plate 58. The end of the sample paper 110 on the turnable cylinder 34a is then fixed by screwing the screw 46a so that the press bar 40a tightly presses the paper against the pad 36a. For precise results, the sample paper 110 should be then placed under light tension and the first gripping means 12 should be adjusted to grip the paper tightly. As shown in FIG. 7, the pendulum 18 is then moved to its ready or start position by rotating the knob 56 at which position the pendulum snaps into the locking means 78. With this action, the sample paper 110 is bent up in a loose way as shown in FIG. 7. The indicator needle 96 is then manually turned counterclockwise to its start position by the knob 102. The pendulum 18 is then released and it swings down through its vertical or rest position thereby causing a sudden bursting action of the paper sample 110 along the line of perforations 112. This is shown in FIG. 8. The pendulum 18 will continue beyond its vertical position to a position that depends upon the amount of energy remaining in the pendulum after the bursting of the paper. The pendulum 18 actuates the indicator needle 96 which will show the maximum position reached by the pendulum. The indication on the readout scale is a measurement for the percentage of energy absorbed by the bursting action of the pendulum.

Thus, the described test apparatus uses the moving energy of the pendulum, which can be defined precisely, to burst the line of perforations with a reproducible power and under conditions equal to those which occur in use of the forms. The test apparatus produces reproducible results within tight tolerances for equal paper material and perforations. Accuracy of measurement and the ability to determine very small differences are high. The test apparatus enables the user to establish minimum and maximum readouts for the burst-resistance of a form according to the handling methods of the forms user and to simulate these methods exactly. The apparatus enables the printer to choose within the minimum and maximum limits the optimum perforating blade or wheel for his production machinery and papers before going into production. The apparatus can accurately measure the final effect of a folded cross perforation produced by a press or collator and determine the weakening effect caused by the folding. The apparatus permits control of the production with prescribed standards of burst-resistance.

A perforating apparatus which may be used with the test apparatus to provide sample lines of perforation is shown in FIGS. 9 and 10. The perforating unit includes a base 120 having mounted thereon a pair of spaced U-shaped standards 122 and a pair of spaced horizontally extending plates 123 which serve as a bed for a paper sample 125. A pair of spaced, parallel, and horizontally extending rods 124 are fixedly attached to the legs of the standards 122. A carriage 126 is carried by the rods 124 for horizontal movement. The carriage carries a wheel 128 which is rotatably mounted to a lower end of an arm of a bell crank 130 that is pivotally mounted to the carriage. The other arm of the bell crank 130 bears against an adjustable pressure screw 132 which is locked in position by a lock screw 133. An elongated replaceable perforating blade 134 is disposed within a slot 136 in a holder 138 mounted to the base in the space between the bed plates 123. The blade 134 is maintained in the holder by a blade holder screw 140. To exchange blades 134, a screw 142 which limits leftward travel of the carriage 126 is removed and the carriage is moved onto the left standard 122. The blade holder screw 140 is loosened and then the blade may be lifted out of its holder.

The wheel 128 is arranged so that when the carriage 126 is moved manually, the wheel rides over the perforating blade 134 thereby perforating a form 125 disposed between the perforating blade 134 and the wheel 128. To adjust the pressure exerted by the wheel, the pressure screw 132 is adjusted.

By varying the perforating blade 134 and the pressure exerted by the roller 128 various lines of perforations may be obtained. By perforating across the grain or with the grain, the user can establish, prior to production, both vertical and horizontal perforations.

The above-described apparatus offers the ideal base to establish statistically and test technically proven quality standards for perforations and for the control of production according to these standards. The apparatus makes possible the establishment of commonly useable standards in the selection of forms perforations both prior to production and after production takes place.

Various changes and modifications may be made in the above-described apparatus without deviating from the spirit or scope of the present invention. Various features of the invention are set forth in the accompanying claims.

What is claimed is:

1. Apparatus for testing the burst strength of a line of perforations in a paper comprising a frame, first means fixedly mounted on said frame for gripping said paper on one side of said line of perforations, second means rotatably mounted on said frame in spaced relation to said first means for gripping said paper on the other side of said line of perforations, a pendulum attached to said second means for causing rotation thereof when said pendulum is swung, said pendulum being swung from a start position where energy is stored in said pendulum, through a second position where the paper is rendered taut and the line of perforations is burst and to a position where the energy remaining in the pendulum after the bursting action is dissipated, and an indicating means actuated by said pendulum for indicating the amount of energy remaining in the pendulum after the bursting action.

2. Apparatus in accordance with claim 1 wherein the first and second gripping means each includes a cylinder and means for pressing the paper against the cylinder to thereby grip the paper.

3. Apparatus in accordance with claim 2 wherein a plate is disposed between the two gripping means which plate bears a reference line for adjusting the line of perforations when inserting the paper.

4. Apparatus in accordance with claim 1 wherein a plate is disposed between the two gripping means which plate bears a reference line for adjusting the line of perforations when inserting the paper.

5. Apparatus in accordance with claim 1 wherein the indicating means includes an L-shaped bolt carried by the rotatable gripping means and a needle which is acted upon by the bolt in order to turn the needle according to movement of the pendulum.

6. Apparatus in accordance with claim 5 wherein the indicating means includes an L-shaped bolt carried by the rotatable gripping means and a needle which is acted upon by the bolt in order to turn the needle according to movement of the pendulum.

7. Apparatus in accordance with claim 6 wherein a snap-locking device is provided wherein the pendulum snaps in and out in its start position.

8. Apparatus in accordance with claim 1 wherein a locking device is provided wherein the pendulum is locked in a vertical rest position in a releasable manner.

9. Apparatus in accordance with claim 8 wherein a locking device is provided wherein the pendulum is locked in a vertical rest position in a releasable manner.

10. Apparatus in accordance with claim 1 wherein a snap-locking device is provided wherein the pendulum snaps in and out in its start position.

* * * * *